United States Patent [19]

Hutchison

[11] Patent Number: 4,801,605
[45] Date of Patent: Jan. 31, 1989

[54] 3-AMINO-DIHYDRO-[1]-BENZOPYRANS AND BENZOTHIOPYRANS

[75] Inventor: Alan J. Hutchison, Verona, N.J.

[73] Assignee: Ciba-Geigy Corporation, Ardsley, N.Y.

[21] Appl. No.: 20,054

[22] Filed: Feb. 27, 1987

Related U.S. Application Data

[63] Continuation-in-part of Ser. No. 902,281, Aug. 29, 1986, abandoned, which is a continuation-in-part of Ser. No. 679,182, Dec. 7, 1984, abandoned, and a continuation-in-part of Ser. No. 772,068, Sep. 3, 1985, abandoned.

[51] Int. Cl.$^4$ .................. A61K 31/38; C07D 335/06; C07D 409/02
[52] U.S. Cl. ................... 514/432; 549/404; 549/23; 548/525; 546/202; 540/596; 514/422; 514/324; 514/212
[58] Field of Search .............. 549/404, 23; 548/525; 546/202, 196; 540/596; 514/456, 432, 422, 324, 320, 212

[56] References Cited

U.S. PATENT DOCUMENTS

| | | | |
|---|---|---|---|
| 3,142,682 | 7/1964 | Stevens | 260/295 |
| 3,607,886 | 9/1971 | Lockhart | 549/404 |
| 3,629,289 | 12/1971 | Lockhart | 549/404 |
| 4,013,771 | 3/1977 | Brown et al. | 549/23 |
| 4,041,079 | 9/1977 | Sugihara et al. | 549/401 X |
| 4,110,347 | 8/1978 | Watts | 549/404 |
| 4,203,895 | 5/1980 | Parcell et al. | 549/404 |
| 4,221,806 | 9/1980 | Ferrini | 549/28 |
| 4,446,113 | 5/1984 | Evans et al. | 549/345 |
| 4,497,820 | 2/1985 | Merlini et al. | 514/432 |
| 4,500,545 | 2/1985 | Bach et al. | 514/619 |
| 4,604,397 | 8/1986 | Hutchison | 514/291 |
| 4,657,925 | 4/1987 | Horn | 514/438 |

FOREIGN PATENT DOCUMENTS

| | | |
|---|---|---|
| 0072070 | 2/1983 | European Pat. Off. |
| 0205264 | 12/1986 | European Pat. Off. |
| 1465838 | 1/1967 | France |
| 59-110690 | 6/1984 | Japan |
| 81/00155 | 12/1981 | PCT Int'l Appl. |

OTHER PUBLICATIONS

I. Lockhart et al., J. Med. Chem., vol. 15, No. 8, 863 (1972).
H. Booth et al., J. Chem. Soc., Perkin II 1973, 227.
M. Stanley et al., Psychopharmacology 66, 23 (1979).
H. Sugihara et al., Chem. Pharm. Bull. 25, 859 (1977).
J. G. Cannon et al., Derivatives of 5-Hydroxy-6-Methyl-2-Aminotetralin, J. Med. Chem. 23, 750–754 (1980).
L. E. Arvidsson et al., 8-Hydroxy-2-(ki-n--propylamino)tetralin, J. Med. Chem 24, 921–923 (1981).
L. E. Arvidsson et al., 8-Hydroxy-2-(alkylamino)tetralins and Related Compounds, J. Med. Chem. 27, 45–51 (1984).
U. Hacksell et al., J. Med. Chem 22, 1469–1475 (1979).
N. Sarda et al., Eur. J. Med. Chem. Chimica Therapeutica 11, 257–262 (1976).
N. Sarda et al., Eur. J. Med. Chem.-Chimica Therapeutica 11, 251–256 (1976).
A. S. Horn et al., J. Med. Chem. 27, 1340–1343 (1984).
Chem. Abstracts 73, 120458j (1970).
Chem. Abstracts 99, 158472j (1983).
J. Org. Chem. 1970, 35 (10), 3495–9.
J. Med. Chem. 21 (7), 643–9 (1978), Abstract.
Synthesis (1976), 409.
Acta Chemica Scandinavica B35, 197 (1981).
Mol. Pharmacol. 26 (3), 452–7 (1984) (Abstract).
Europ. J. Pharmacol. 99 (1), 125–126 (1984 (Abstract).
J. Indian Chemical Society 43 (7), 521 (1966).
J. M. Cossery et al., European J. Pharmacology 140, 143 (1987).
J. C. Berry et al., Poster presented at Federation Meetings, Apr. 23, 1985.
J. C. Berry et al., Society for Neuroscience Abstracts, Nov. 1987 Meeting, Abstract No. 128.20.
W. C. Boyar et al., Poster Presented at Society for Neuroscience Meeting (Soc. Neuroscience Abstracts) 12, 1236 (1986).
J. Med. Chem. 27, pp. 45–51 (1984).
Fed. Proceedings, 44 (4), 1985, p. 891, Abstract No. 2807.

*Primary Examiner*—Nicky Chan
*Attorney, Agent, or Firm*—Norbert Gruenfeld

[57] ABSTRACT

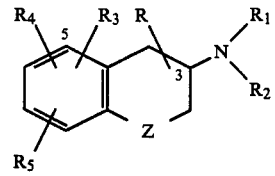

(I)

wherein Z represents O or S; R represents hydrogen or lower alkyl; $R_1$ represents hydrogen, lower alkyl or aryl-lower alkyl; $R_2$ represents hydrogen, lower alkyl or aryl-lower alkyl; or $R_1$ and $R_2$ together represent alkylene of 4 to 6 carbon atoms; $R_3$ represents hydrogen, hydroxy, lower alkoxy, aryl-lower alkoxy, acyloxy or aryloxy in compounds wherein Z represents S; or $R_3$ represents hydroxy, lower alkoxy, aryl-lower alkoxy, acyloxy or aryloxy, and is attached only at the 5- or 8-position in compounds wherein Z represents O; $R_4$ and $R_5$ represent independently hydrogen, lower alkyl or halogen; and pharmaceutically acceptable salts thereof; and mono or di- S-oxides of compounds of formula I wherein Z represents S and pharmaceutically acceptable salts thereof, pharmaceutical compositions thereof; and use thereof as central nervous system active agents for the treatment of central nervous system disorders.

11 Claims, No Drawings

3-AMINO-DIHYDRO-[1]-BENZOPYRANS AND BENZOTHIOPYRANS

CROSS-REFERENCE TO RELATED APPLICATIONS

This application is a continuation-in-part of application Ser. No. 902,281, filed Aug. 29, 1986, now abandoned, which is a continuation-in-part of both applications Ser. No. 679,182 filed Dec. 7, 1984 (now abandoned), and Ser. No. 772,068 filed Sept. 3, 1985 (now abandoned).

SUMMARY OF THE INVENTION

The present invention is concerned with certain 3,4-dihydro-2H-[1]-(benzopyran and benzythiopyran)-3-amines useful as central nervous system receptor modulators, particularly serotonin receptor agonists, for the treatment of central nervous system disorders, particularly depression and anxiety, processes for preparing same, pharmaceutical compositions comprising said compounds, and methods of stimulating serotonin receptors in mammals and of treating syndromes, conditions and diseases in mammals responsive to the effect of such serotonin receptor agonist by administration of a said compound or a pharmaceutical composition comprising a said compound.

DETAILED DESCRIPTION OF THE INVENTION

Particularly the invention is concerned with the novel 3,4-dihydro-2H-[1]-benzopyran-3-amine and 3,4-dihydro-2H-[1]-benzothiopyran-3-amine derivatives of formula I

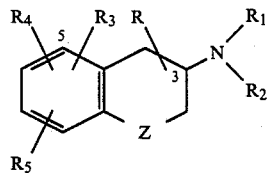

wherein Z represents O or S; R represents hydrogen or lower alkyl; $R_1$ represents hydrogen, lower alkyl or aryl-lower alkyl; $R_2$ represents hydrogen, lower alkyl or aryl-lower alkyl; or $R_1$ and $R_2$ together represent alkylene of 4 to 6 carbon atoms; $R_3$ represents hydrogen, hydroxy, lower alkoxy, aryl-lower alkoxy, acyloxy or aryloxy in compounds wherein Z represents S; or $R_3$ represents hydroxy, lower alkoxy, aryl-lower alkoxy, acyloxy or aryloxy, and is attached only at the 5- or 8-position in compounds wherein Z represents O; $R_4$ and $R_5$ represent independently hydrogen, lower alkyl or halogen; and pharmaceutically acceptable salts thereof; and mono or di- S-oxides of compounds of formula I wherein Z represents S and pharmaceutically acceptable salts thereof.

A particular embodiment of the invention is represented by the compounds (of formulae I, IA and IB as defined herein) wherein Z represents S; mono- or di-S-oxides thereof; and pharmaceutically acceptable salts of any said compounds.

Another particular embodiment of the invention is represented by the compounds (of formulae I, IA and IB as defined herein) wherein Z represents O; and pharmaceutically acceptable salts thereof.

Preferred are the compounds of formula I wherein the group $R_3$ is attached at the 5-position.

More particularly the invention relates to the compounds of formula IA

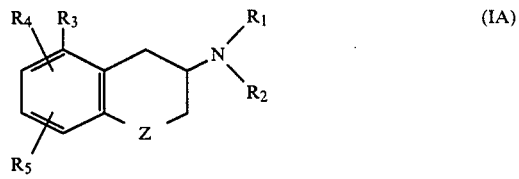

wherein Z represents O or S; $R_1$ represents hydrogen, lower alkyl or aryl-lower alkyl; $R_2$ represents hydrogen, lower alkyl or aryl-lower alkyl; or $R_1$ and $R_2$ together represent alkylene of 4 to 6 carbon atoms; $R_3$ represents hydrogen, hydroxy, lower alkoxy, aryl-lower alkoxy; or $R_3$ represents hydroxy esterified in form of a pharmaceutically acceptable ester; $R_4$ and $R_5$ independently represent hydrogen, lower alkyl or halogen; pharmaceutically acceptable salts thereof; and mono or di S-oxides of compounds of formula IA and pharmaceutically acceptable salts thereof wherein Z represents S.

Preferred are the compounds of formula IA wherein Z represents O or S; $R_1$ represents hydrogen or lower alkyl; $R_2$ represents lower alkyl or aryl-lower alkyl; or $R_1$ and $R_2$ together represent butylene or pentylene; $R_3$ represents hydroxy, lower alkoxy or benzyloxy; or $R_3$ represents hydroxy esterified in form of a pharmaceutically acceptable ester; $R_4$ represents hydrogen, halogen or lower alkyl; $R_5$ represents hydrogen; and pharmaceutically acceptable salts thereof.

Further preferred are the compounds of formula IA wherein Z represents O or S; $R_1$ and $R_2$ represent lower alkyl of 1 to 4 carbon atoms; $R_3$ represents hydroxy, lower alkoxy of 1 to 4 carbon atoms or benzyloxy; or $R_3$ represents hydroxy esterified in form of a pharmaceutically acceptable ester; $R_4$ is attached at the 7 or 8 position and represents hydrogen, lower alkyl of 1 to 4 carbon atoms or halogen; $R_5$ represents hydrogen; and pharmaceutically acceptable salts thereof.

A particular embodiment relates to the above-cited compounds of formula IA wherein Z represents oxygen (O). Another embodiment relates to the above-cited compounds of formula IA wherein Z represents sulfur (S). Preferred are the compounds of formula IA wherein Z represents S.

Preferred in turn are the compounds of formula IB

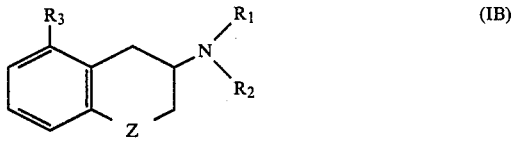

wherein Z represents O or S; $R_1$ represents hydrogen or lower alkyl; $R_2$ represents lower alkyl, benzyl or phenethyl; $R_3$ represents hydroxy, lower alkoxy or benzyloxy; or $R_3$ represents hydroxy esterified in form of a pharmaceutically acceptable ester; and pharmaceutically acceptable salts thereof.

Further preferred are the compounds of formula IB wherein Z represents O or S; $R_1$ and $R_2$ represent lower alkyl; $R_3$ represents hydroxy, lower alkoxy or benzyloxy; or $R_3$ represents hydroxy esterified in form of a pharmaceutically acceptable ester; and pharmaceutically acceptable salts thereof.

Particulary preferred are the compounds of formula IB wherein Z represents O or S; $R_1$ and $R_2$ are identical and represent straight chain alkyl of 1 to 4 carbon atoms; $R_3$ represents hydroxy or alkoxy of 1 to 4 carbon atoms; and pharmaceutically acceptable salts thereof. Especially preferred are the compounds of formula IB wherein $R_3$ represents alkoxy of 1 to 4 carbon atoms.

A particular embodiment relates to the above-cited compounds of formula IB wherein Z represents oxygen (O). Another embodiment relates to the above-cited compounds of formula IB wherein Z represents sulfur (S). Preferred are the compounds of formula IB wherein Z represents S.

A further specific embodiment of the invention relates to the compounds of formula I wherein Z represents O; $R_3$ is hydroxy located at the 5- or 8-position; $R_1$ and $R_2$ represent lower alkyl of 1 to 3 carbon atoms; R, $R_4$ and $R_5$ represent hydrogen; pharmaceutically acceptable prodrug esters thereof; and pharmaceutically acceptable salts thereof.

A further specific embodiment thereof relates to the compounds of formula I wherein Z represents O; $R_1$ and $R_2$ represent lower alkyl of 1 to 3 carbon atoms; R, $R_4$ and $R_5$ represent hydrogen; $R_3$ represents lower alkoxy or aryl-lower alkoxy located at the 5- or 8-position; and pharmaceutically acceptable salts thereof.

The general definitions used herein have the following meaning within the scope of the present invention.

The term "lower" referred to above and hereinafter in connection with organic radicals or compounds respectively defines such with up to and including 7, preferably up to and including 4 and advantageously one or two carbon atoms.

A lower alkyl group contains 1 to 7 carbon atoms, preferably 1 to 4 carbon atoms, is advantageously straight chain and represents for example methyl, ethyl, propyl or butyl.

Aryl is preferably phenyl or phenyl substituted preferably by one to three of lower alkyl, halogen or lower alkoxy; or aryl is heteroaryl, preferably pyridyl.

Aryl-lower alkyl is preferably benzyl or 2-phenylethyl, optionally substituted on phenyl as defined for aryl.

Lower alkoxy is preferably alkoxy of 1 to 4 carbon atoms, advantageously straight chain.

Aryl-lower alkoxy is preferably phenyl-lower alkoxy of 1 to 4 carbon atoms, advantageously straight chain, optionally substituted on phenyl as defined for aryl.

Aryloxy is preferably phenoxy.

Hydroxy esterified in form of a pharmaceutically acceptable ester represents acyloxy as defined herein.

Acyloxy is preferably hydroxy esterified in the form of a pharmaceutically acceptable ester and represents preferably lower alkanoyloxy, aroyloxy, lower alkoxycarbonyloxy, carbamoyloxy or mono- or di-lower alkylcarbamoyloxy.

Lower alkanoyloxy is preferably acetoxy, pivaloyloxy (trimethylacetoxy) or propionyloxy.

Aroyloxy is preferably benzoyloxy or benzoyloxy substituted on the benzene ring by one to three of lower alkyl, lower alkoxy, halogen or trifluoromethyl, or heteroaroyloxy.

Heteroaroyloxy is preferably thienoyloxy, pyrroloyloxy or 2-, 3- or 4-pyridylcarbonyloxy, advantageously nicotinoyloxy.

Lower alkoxycarbonyloxy is preferably methoxycarbonyloxy, ethoxycarbonyloxy, propoxycarbonyloxy or butoxycarbonyloxy.

Mono- or di-lower alkylcarbamoyloxy is preferably mono- or di-N-(methyl, ethyl, propyl)-carbamoyloxy.

Halogen is preferably fluoro or chloro, but may also be bromo or iodo.

The pharmaceutically acceptable esters represented by compounds of formula I, IA or IB wherein $R_3$ represents hydroxy esterified in form of pharmaceutically acceptable ester, are particularly prodrug esters that may be convertible by solvolysis under physiological conditions to the compounds of formula I, IA or IB wherein $R_3$ represents hydroxy.

Preferred prodrug pharmaceutically acceptable esters are straight chain or branched lower alkanoyl esters, e.g., the acetyl, isobutyryl, pivaloyl ester; aroyl esters, e.g., the benzoyl, nicotinoyl ester; carbamoyl esters (carbamates), e.g. the mono- or di-ethylcarbamoyl or N-mono- or di-methylcarbamoyl ester. Most preferred are the lower alkanoyl esters.

Depending on the definition of R and the resulting number of asymmetric carbon atoms, the compounds of formula I exist in the form of stereoisomers, e.g. diasteroisomers, racemates, pure enantiomers or mixtures thereof, all of which are within the scope of the invention.

Pharmaceutically acceptable salts are therapeutically acceptable acid addition salts, preferably salts of inorganic or organic acids, such as strong mineral acids, for example hydrohalic, e.g. hydrochloric or hydrobromic acid; sulfuric, phosphoric or nitric acid; aliphatic or aromatic carboxylic or sulfonic acids, e.g. formic, acetic, propionic, succinic, glycollic, lactic, malic, tartaric, gluconic, citric, maleic, fumaric, pyruvic, phenylacetic, benzoic, 4-aminobenzoic, anthranilic, 4-hydroxybenzoic, salicylic, 4-aminosalicylic, pamoic, nicotinic, methanesulfonic, ethanesulfonic, hydroxyethanesulfonic, benzenesulfonic, p-toluenesulfonic, naphthalenesulfonic, sulfanilic, cyclohexylsulfamic acid; or ascorbic acid.

The novel compounds of the invention are active in state of art in vitro and in vivo test systems which are correlated with effectiveness for the treatment of central nervous system disorders in mammals, including man.

The compounds of the invention are active as selective serotonin (S) receptor stimulants (agonists) in mammals, with selectivity for the S-1 receptor, and particularly the S-1A receptor.

Thus the compounds of this invention possess valuable pharmacological properties in mammals, primarily serotonin (S) receptor stimulating (agonistic) properties indicative of e.g. anxiolytic and psychostimulant (antidepressant) activity. Particularly preferred are the compounds of formula IA and IB.

The above-cited properties are demonstrable in vitro and in vivo tests, using advantageously mammals, e.g. rats, dogs, monkeys or isolated organs, tissues and enzyme preparations thereof. Said compounds can be applied in vitro in the form of solutions, e.g. preferably aqueous solutions, and in vivo either enterally or parenterally, advantageously orally or intravenously, e.g. within gelatin capsules, as starch suspensions or in aqueous solutions. The dosage in vitro may range between about $10^{-4}$ molar and $10^{-9}$ molar concentrations. The dosage in vivo may range preferably between about 0.05 and 30 mg/kg/day, advantageously between about 0.10 and 15 mg/kg/day.

The serotonin (S-1A) binding properties indicative of serotonin agonistic receptor regulating activity for the compounds of the invention are determined in the in vitro binding assay as follows:

Membrane suspensions are prepared from rat brain and incubated with $^3$H-serotonin by a modification of the procedure described by Martin and Sanders-Bush, Naunyn-Schmiedeberg's Arch. Pharmacol 321, 165 (1982) and by Middlemiss and Fozard, Eur. J. Pharmacol. 90, 151 (1983).

In the binding assay, 0.85 ml aliquots of the tissue suspension are added to tubes containing $^3$H-serotonin with or without test compound dissolved in buffer. The final concentration of $^3$H-serotonin is 2 nM. Test compounds are evaluated over a wide range of concentration. The IC$_{50}$ values (concentrations of test compounds required to inhibit the specific binding of 2 nM $^3$H-serotonin by 50%) are determined graphically.

Illustrative of the invention, 5-hydroxy-3,4-di-hydro-N,N-dipropyl-2H-[1]-benzothiopyran-3-amine hydrochloride has an IC$_{50}$ of about $2.6 \times 10^{-9}$M, 5-ethoxy-3,4-di-hydro-N,N-dipropyl-2H-[1]-benzothiopyran-3-amine hydrochloride has an IC$_{50}$ of about $2.1 \times 10^{-8}$M, and 5-ethoxy-N,N-dipropyl-3,4-dihydro-2H-[1]-benzopyran-3 amine hydrochloride has an IC$_{50}$ of about $4.0 \times 10^{-8}$M in the $^3$H-serotonin (S-1A) binding assay.

The serotonin receptor agonist activity is determined in vivo by measuring the decrease in the accumulation of 5-hydroxytryptophane in the brain after administration of a test compound in the rat, as described in J. Med. Chem. 21, 864 (1978).

Illustrative of the invention, 5-ethoxy-3,4-dihydro-N,N-dipropyl-2H-[1]-benzothiopyran-3-amine hydrochloride decreases the accumulation of 5-hydroxytryptophane in the cortex of the brain in the rat by about 25% when administered at a dose of about 2.7 mg/kg p.o.

The aforesaid advantageous properties render the compounds of the invention useful as therapeutic agents in mammals, especially as central nervous system active agents. The compounds of the invention are primarily useful as serotonin agonists and are of interest e.g. as psychostimulants for the treatment of depression, cognition deficiencies (senile dementia) and minimal brain dysfunction, as anxiolytics for the treatment of anxiety, and as appetite suppressants for the treatment of obesity in mammals.

Preferred as selective serotonin (S-1A) agonists are the compounds of formula IA and particularly those of formula IB.

Certain compounds of the invention, particularly compounds of formula I wherein R$_3$ (when applicable) is attached at the 6, 7 or 8 position, also demonstrate presynaptic dopamine receptor stimulating (agonistic) properties indicative of neuroleptic (antipsychotic) properties.

The presynaptic dopamine receptor binding properties indicative of presynaptic dopamine receptor agonistic activity are determined in the dopamine binding assay in vitro by the standard method involving the displacement of the dopamine agonist 2-amino-6,7-dihydroxy-1,2,3,4-tetra-hydro-naphthalene ($^3$H-ADTN) from membranes of calf-caudate nucleus.

Illustrative of the invention, 8-hydroxy-3,4-di-hydro-N,N-dipropyl-2H-[1]-benzopyran-3-amine hydrochloride has an IC$_{50}$ of about $2 \times 10^{-8}$M in the $^3$H-ADTN dopamine receptor assay.

The in-vivo presynaptic dopamine agonist activity (also called dopamine autoreceptor agonist activity) is determined in the rat gamma-butyrolactone (GBL) model by a modification of the procedure desribed by Walters and Roth, Naunyn Schmiedeberg;s Arch. Pharmacol. 296, 6 (1976). In this model, a presynaptic dopamine agonist inhibits the GBL-induced accumulation of the dopamine precursor DOPA in the brain after pretreatment with 3-hydroxy-benzylhydrazine (NDS-1015), a DOPA decarboxylase inhibitor.

Compounds demonstrating presynaptic dopamine receptor agonist activity are useful for the treatment of psychotic conditions, parkinsonism and dyskinesias.

The compounds of the invention are prepared using processes which comprise:

(a) condensation of a compound of the formula II

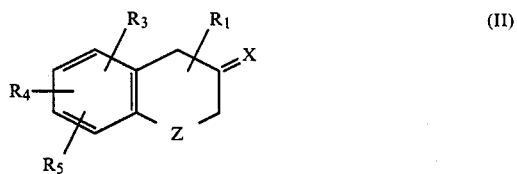

wherein Z, R, R$_3$–R$_5$ have meaning as previously defined above, X represents oxo, or X represents reactive esterified hydroxy together with hydrogen; or of a mono- or di-S-oxide of a compound of formula II wherein Z represents S, with a compound of the formula III

wherein R$_1$ and R$_2$ have meaning as previously defined; or (b) alkylation of a compound of the formula IV

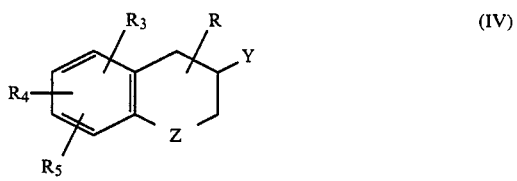

wherein Z, R, R$_3$–R$_5$ have meaning as defined above, and Y represents NH$_2$, NHR$_1$ or NHR$_2$, with a reactive ester derivative of the lower alkanol

R$_1$—OH or R$_2$—OH (V)

wherein R$_1$ and R$_2$ have meaning as previously defined, or with an aldehyde corresponding to R$_1$—OH or R$_2$—OH, under reductive conditions; or (c) cleaving a compound of formula VI

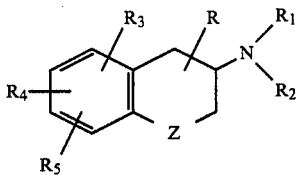

wherein Z, R₁, R₂, R₄ and R₅ have meaning as defined above and R₃ represents etherified hydroxy, to obtain a compound of formula I wherein R₃ represents hydroxy; and, if desired, acylating a said compound of formula I wherein R₃ represents hydroxy to a compound of formula I wherein R₃ represents acyloxy; or, if desired, converting a said compound of formula I wherein R₃ represents hydroxy to a compound of formula I wherein R₃ represents lower alkoxy or aryl-lower alkoxy; or (d) reducing a compound of the formula VII

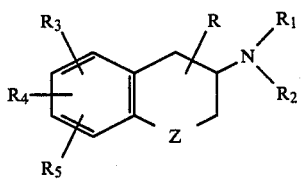

wherein Z, R, R₁-R₅ have meaning as defined above, and the bonds with dotted lines represent a double bond situated at any of the indicated positions;

(e) reducing a compound of formula VIII

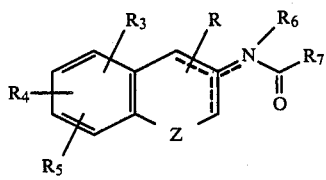

wherein R₆ represents R₁ or R₂; Z, R, R₁-R₅ have meaning as defined above; and R₇ represents lower alkyl with 1 to 6 carbon atoms, aryl-lower alkyl with 1 to 6 carbon atoms, or hydrogen; and, if necessary, temporarily protecting any interfering reactive group(s) in all these processes, and then isolating the resulting compound of the formula I; and, if desired, converting a resulting compound of formula I into another compound of the invention, and/or, if desired, converting a resulting free compound into a salt or a resulting salt into a free compound or into another salt, and/or, if required, separating a mixture of isomers or racemates obtained into the single isomers or racemates, and/or, if desired, resolving a racemate obtained into the optical antipodes.

A reactive esterified hydroxy group (reactive ester of an alcohol) in any of the above mentioned processes is hydroxy esterified by a strong acid, especially a strong inorganic acid, such as a hydrohalic acid, especially hydrochloric, hydrobromic or hydriodic acid, or sulphuric acid, or by a strong organic acid, especially a strong organic sulfonic acid, such as an aliphatic or aromatic sulfonic acid, for example methanesulfonic acid, 4-methylphenylsulfonic acid or 4-bromophenylsulfonic acid. Said reactive esterified hydroxy group is especially halo, for example chloro, bromo or iodo, or aliphatically or aromatically substituted sulfonyloxy, for example methylsulfonyloxy or 4-methylphenylsulfonyloxy (tosyloxy).

Etherified hydroxy as indicated for R₄ in the above mentioned process (c) represents, for instance, lower alkoxy, such as methoxy or ethoxy; benzyloxy unsubstituted or substituted on the phenyl ring e.g. by lower alkyl, halogen or lower alkoxy, such as methyl, chloro or methoxy respectively; pyridyl-lower alkoxy, e.g. pyridylmethoxy.

In starting compounds and intermediates which are converted to the compounds of the invention in a manner described herein, functional groups present, such as amino and hydroxy, are optionally protected by conventional protecting groups that are common in preparative organic chemistry. Protected amino and hydroxy groups are those that can be converted under mild conditions into free amino and hydroxy groups without the molecular framework being destroyed or other undesired side reactions taking place.

Well-known protecting groups that meet these conditions and their introduction and removal are described, for example, in J. F. W. McOmie, "Protective Groups in Organic Chemistry", Plenum Press, London, New York 1973, T. W. Greene, "Protective Groups in Organic Synthesis", Wiley, N.Y. 1981, and also in Houben-Weyl, "Methoden der Organischen Chemie", Vol. 15/1, George Thieme Verlag, Stuttgart, 1974.

The preparation of the compounds of the invention according to process (a) is carried out according to procedures known in the art for N-alkylation reactions.

The preparation of compounds of the invention by reductive N-alkylation when X represents oxo is carried out under conditions known to the art, e.g. with chemical reducing agents such as hydride reducing agents, advantageously an alkali metal cyanoborohydride such as sodium cyanoborohydride. The reductive amination with an alkali metal cyanoborohydride is preferably carried out in an inert solvent, e.g. methanol or acetonitrile, advantageously in the presence of an acid, e.g. hydrochloric acid or acetic acid.

The preparation of the compounds of the invention by process (a) when X represents reactive esterified hydroxy together with hydrogen is carried out with or without basic catalysts such as triethylamine or potassium carbonate in an inert solvent, under conditions well-known in the art for N-alkylation reactions.

The preparation of the compounds of the invention according to process (b) is carried out under conditions described above for process (a), e.g. for N-alkylation when the starting material is a reactive ester of R₁—OH or R₂—OH, and under conditions described under process (a) for reductive N-alkylation when the starting material is an aldehyde (a lower alkylcarboxaldehyde or an aryl-lower alkylcarboxaldehyde).

The preparation of the compounds of the invention represented by formula I wherein R₃ is hydroxy from compounds of formula VI wherein R₃ represents etherified hydroxy, according to process (c), is carried out by methods well-known in the art, e.g., with a mineral acid, such as hydriodic acid and, advantageously from compounds wherein R₃ is lower alkoxy, particularly methoxy, with e.g. sodium or lithium diphenylphosphide in tetrahydrofuran at reflux temperature, or with boron tribromide in methylene chloride.

Starting with compounds of formula VI wherein Z represents O and R₃ represents optionally substituted benzyloxy, the preparation according to process (c) is advantageously carried out by hydrogenolysis using hydrogen in the presence of a catalyst, e.g. palladium, under conditions well-known in the art.

The preparation of the compounds of the invention according to process (d) is carried out according to procedures known in the art for the saturation of carbon to nitrogen or enamine carbon to carbon double bonds, e.g. with a chemical reducing agent such as sodium cyanoborohydride under conditions known in the art e.g. at room or elevated temperature in a polar solvent such as isopropanol.

The preparation of the compounds of the invention wherein Z represents O according to process (d) is also carried out with hydrogen, preferably in the presence of a catalyst such as palladium or charcoal.

The preparation of the compounds of the invention according to process (e) is carried out according to procedures known in the art for the reduction of an amide group, e.g. by reduction with a hydride reducing agent e.g. lithium aluminum hydride or borane (diborane) in an inert solvent such as tetrahydrofuran or diethyl ether, advantageously at room or elevated temperature.

The starting materials of formula II are known in the art or can be prepared according to methods known in the art.

The starting materials of formula II wherein Z represents S, the optionally substituted 3,4-dihydro-2H-[1]-benzothiopyran-3-ones (thiochroman-3-ones) can be prepared according to methods known in the art e.g. according to J. Org. Chem. 34, 1566 (1969), or as illustrated in the examples.

The starting materials of formula II wherein Z represents O, the substituted chroman-3-ones, can be prepared according to methods known in the art for the synthesis of 3-chromanones, e.g. according to J. Chem. Soc. 1610 (1948), J. Am. Chem. Soc. 87, 3958 (1965) and Bull. Soc. Chim. Belg. 82, 283 (1973), or as illustrated in the examples.

For example, according to the method described in Bull. Soc. Chim. Belg. 82, 283 (1973), an appropriately lower alkoxy or benzyloxy substituted salicyladehyde or thiosalicyladehyde, is condensed with a lower alkyl ester of acrylic acid to yield the correspondingly substituted 2H-[1]-(benzopyran- or benzothiopyran)-3-carboxylic acid. Curtius degradation to the correspondingly substituted 3-amino-2H-[1]-(benzopyran or benzothiopyran), followed by acidic hydrolysis yields the correspondingly substituted chroman-3-one or thiochroman-3-one intermediate.

The starting materials of formula II, particularly wherein Z represents O, can also be advantageously prepared by the following novel process, as illustrated below:

An appropriately lower alkoxy or benzyloxy substituted 2H-[1]-benzopyran, e.g. as described in J. Org. Chem. 38, 3832 (1973), is reacted with a halogenating agent, e.g. N-bromosuccinimide or N-bromoacetamide in a hydroxylating solvent such as aqueous acetone to give the correspondingly substituted 3-halo-4-hydroxychroman, specifically 3-bromo-4-hydroxychroman. Reaction with a nonaqueous base, e.g. sodium hydride in tetrahydrofuran, results in the formation of the correspondingly substituted chroman-3,4-epoxide. Rearrangement with an acidic reagent, advantageously zinc iodide in toluene, results in the isolation of the lower alkoxy or benzyloxy substituted chroman-3-one intermediate.

The starting materials of formula II wherein Z represents S can be converted to the mono- or di-S-oxides thereof by treatment with e.g. a peracid, preferably m-chloroperbonzoic acid, to obtain either the mono-S-oxide (sulfoxide) or di-S-oxide (sulfone) depending on the quantity of peracid used. The sulfoxides may also be prepared by treatment with a salt of periodic acid, e.g. sodium periodate.

The hydroxy substituted chroman-3-ones and thiochroman-3-ones are preferably prepared by cleavage of e.g. the corresponding lower alkyl ethers, benzyl ethers, advantageously by cleavage of the methyl ether derivatives thereof, with reagents known in the art for cleaving said ethers, advantageously lithium diphenylphosphide in refluxing tetrahydrofuran.

The acyloxy substituted 3,4-dihydro-2H-[1]-(benzopyran-3-ones and benzothiopyran)-3-ones can be prepared by acylation of the corresponding hydroxy substituted 3,4-di-hydro-2H-[1]-(benzopyran-3-ones and benzothiopyran)-3-ones using acylation procedures well-known in the art.

The primary and secondary 3-amino-3,4-dihydro-2H-[1]-(benzopyrans and benzothiopyrans) e.g. of formula IV, are prepared from the intermediates of formula II by reaction with ammonia, a primary amine ($R_1NH_2$ or $R_2NH_2$), or preferably an acid addition salt thereof, in the presence of a reducing agent, advantageously sodium cyanoborohydride, when X represents oxo.

Primary 3-amino-3,4-dihydro-2H-[1]-benzopyrans and benzothiopyrans (e.g. of formula IV for process b) may also be prepared by condensing e.g. an optionally substituted phenol or benzenethiol with α-(halomethyl)-acrylic acid followed by cyclization of the resulting α-(phenoxymethyl or benzenethiomethyl)-acrylic acid at elevated temperature to obtain the corresponding optionally substituted 3,4-dihydro-2H-[1]-(benzopyran or benzothiopyran)-3-carboxylic acid. Curtius degradation by reaction with e.g. diphenylphosphonyl azide yields the corresponding optionally substituted 3,4-dihydro-3-amino-2H-[1]-(benzopyran or benzothiopyran).

The intermediates of formula VI for process (c) can be prepared by e.g. reductive amination under conditions described above of the correspondingly substituted 3,4-dihydro-2H-[1]-(benzopyran and benzothiopyran)-3-ones with an amine of the formula III.

The intermediates of formula VII may be prepared by treatment of the correspondingly substituted 3,4-dihydro-2H-[1]-(benzopyran and benzothiopyran)-3-ones with an amine of the formula III under dehydrating conditions, e.g. in the presence of molecular sieves, boron trifluoride etherate or p-toluenesulfonic acid in an inert solvent such as toluene or methylene chloride.

The intermediates of formula VIII may be prepared by acylation of a compound of formula IV wherein Y represents $NHR_1$ or $NHR_2$ with a carboxylic acid of the formula $R_7$-COOH wherein $R_7$ has meaning as defined above, in the presence of a condensing agent such as dicyclohexylcarbodiimide, or with a reactive functional derivative thereof, e.g. an acyl halide such as the acid chloride, or a mixed anhydride, e.g. such derived from a lower alkyl halocarbonate such as ethyl chloroformate, is an inert solvent such as methylene chloride, preferably in the presence of a basic catalyst such as pyridine.

The compounds of the invention obtained by any of the methods described above can be converted into each other according to conventional methods known to the art, and e.g. as illustrated herein.

Compounds of formula I, wherein $R_3$ represents e.g. acyloxy, such as lower alkanoyloxy or aroyloxy, may be converted to compounds of formula I, wherein $R_3$ represents hydroxy by hydrolysis with e.g. aqueous acid such as hydrochloric acid, or with aqueous alkali, such as lithium or sodium hydroxide.

Conversely, the conversion of compounds of formula I, wherein $R_3$ represents hydroxy to compounds of formula I, wherein $R_3$ represents acyloxy, such as alkanoyloxy or aroyloxy, may be carried out by condensation with a corresponding carboxylic acid, or a reactive functional derivative thereof, according to acylation (esterification) procedures well-known to the art.

The conversion of compounds of formula I wherein $R_3$ represents hydroxy to compounds of formula I wherein $R_3$ represents lower alkoxy or aryl-lower alkoxy can be advantageously carried out by condensation with an equivalent amount of a reactive ester of a lower alkanol or aryl-lower alkanol, respectively, (e.g. with a halide such as a lower alkyl or aryl-lower alkyl iodide) in the presence of an equivalent amount of a strong base, such as sodium hydide, in a non-aqueous solvent, such as dimethylsulfoxide or dimethylformamide.

With reference to the above reactions and as mentioned above, it may be advantageous to appropriately protect the potentially reactive, e.g. hydroxy, or other interfering substituents in accordance with protective techniques well-known to the art, e.g. as illustrated below, such that interfering reactions are avoided, by protecting such substituents prior to the desired reaction and subsequently, if necessary removing the protective groups to obtain the desired compounds, e.g. of formula I, or intermediates.

A hydroxy group may be protected in the form of esters, e.g. as acyl derivatives such as the lower alkanoyl, benzyloxycarbonyl or lower alkoxycarbonyl esters, or such hydroxy group may be protected in the form of ethers, e.g. as the 2-tetrahydropyranyl, or benzyl ethers.

In a resulting protected compound of formula I or intermediate, in which one or more of the functional groups are protected, the protected functional groups, e.g. hydroxy groups can be liberated, in a manner, known per se, e.g. by means of solvolysis, especially hydrolysis with acid, or by means of reduction, especially hydrogenolysis, as illustrated herein.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures preferably near the boiling point for the solvents used, at atmospheric or superatmospheric pressure.

The invention further includes any variant of the present processes, in which an intermediate product obtainable at any stage thereof is used as starting material and the remaining steps are carried out, or the process is discontinued at any stage thereof, or in which the starting materials are formed under the reaction conditions, or in which the reaction components are used in the form of their salts or optically pure antipodes. Whenever desirable, the above processes are carried out after first suitably protecting any potentially interfering reactive functional groups, as illustrated above and in the examples herein.

Advantageously, those starting materials should be used in said reactions, that lead to the formation of those compounds indicated above as being preferred.

The invention also relates to novel starting materials and processes for their manufacture.

Depending on the choice of starting materials and methods, the new compounds may be in the form of one of the possible isomers or mixtures thereof, for example, as pure geometric isomers (cis or trans), as pure optical isomers (as antipodes), or as mixtures of optical isomers such as racemates, or as mixtures of geometric isomers.

In case geometric or diastereomeric mixtures of the above compounds or intermediates are obtained, these can be separated into the single racemic or optically active isomers by methods in themselves known, e.g. by fractional distillation, crystallization and/or chromatography.

The racemic products of formula I or basic intermediates can be resolved into the optical antipodes, for example, by separation of diastereomeric salts thereof, e.g., by the fractional crystallization of d- or -(tartrate, dibenzoyltartrate, mandelate or camphorsulfonate) salts.

Advantageously, the more active of the antipodes of the compounds of this invention is isolated.

Finally, the compounds of the invention are either obtained in the free form, or as a salt thereof. Any resulting base can be converted into a corresponding acid addition salt, preferably with the use of a pharmaceutically acceptable acid or anion exchange preparation, or resulting salts can be converted into the corresponding free bases, for example, with the use of a stronger base, such as a metal or ammonium hydroxide, or any basic salt, e.g., an alkali metal hydroxide or carbonate, or a cation exchange preparation. These or other salts, for example, the picrates, can also be used for purification of the bases obtained; the bases are converted into salts. In view of the close relationship between the free compounds and the compounds in the form of their salts, whenever a compound is referred to in this context, a corresponding salt is also intended, provided such is possible or appropriate under the circumstances.

The compounds, including their salts, may also be obtained in the form of their hydrates, or include other solvents used for the crystallization.

The present invention additionally relates to the use in mammals of the compounds of formula I and their pharmaceutically acceptable, non-toxic acid addition salts, or pharmaceutical compositions thereof, as medicaments, especially as neurotropic agents for the treatment of e.g. central nervous system disorders responsive to serotonin receptor stimulation, e.g. depression and anxiety.

The present invention also relates to the use of the compounds of the invention for the preparation of pharmaceutical compositions, especially pharmaceutical compositions having serotonin receptor stimulating activity and useful for the treatment of e.g. depression and anxiety.

The pharmaceutical compositions according to the invention are those suitable for enteral, such as oral or rectal, transdermal and parenteral administration to mammals, including man, for the treatment of diseases responsive to e.g. serotonin receptor stimulation, such as depression and anxiety, comprising an effective amount of a pharmacologically active compound of formula I or a pharmaceutically acceptable salt thereof, in combination with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salts and/or polyethylene glycol; for tablets also c) binders, e.g. magnesium aluminum silicate, starch paste, gelatin, tragacanth, methylcellulose, sodium carboxymethylcellulose and/or polyvinylpyrrolidone; if desired, d) disintegrants, e.g. starches, agar, alginic acid or its sodium salt, or effervescent mixtures; and/or e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, the compositions may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of formula I with carrier. Advantageous carriers include absorbable pharmacologically acceptable solvents to assist passage through the skin of the host. Characteristically, transdermal devices are in the form of a bandage comprising a backing member, a reservoir containing the compound, optionally with carriers, optionally a rate controlling barrier to deliver the compound to the skin of the host at a controlled and predetermined rate over a prolonged period of time, and means to secure the device to the skin.

More specifically, one aspect of the present invention relates advantageously to the method of treatment of central nervous system disorders in mammals e.g. such responsive to serotonin receptor stimulation, for example anxiety, using an effective amount of a compound of the invention, particularly of formula IA or IB, or a pharmaceutically acceptable salt of such compounds as pharmacologically active substances, preferably in the form of above-cited pharmaceutical compositions.

The present invention also relates to the use of compounds of the invention having presynaptic dopamine receptor stimulating properties and pharmaceutical compositions comprising said compounds for the treatment in mammals of central nervous system disorders responsive to presynaptic dopamine receptor stimulation, particularly psychotic conditions (e.g. schizophrenia), parkinsonism and dyskinesias.

The dosage of active compound administered is dependent on the species of warm-blooded animal (mammal), the body weight, age and individual condition, and on the form of administration.

A unit dosage for a mammal of about 50 to 70 kg may contain between about 15 and 200 mg of the active ingredient.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg. Unless mentioned otherwise, an alkyl group, e.g. propyl, refers to n-alkyl, e.g. n-propyl.

EXAMPLE 1

(A) A mixture of 4.6 g of 3,4-dihydro-5-methoxy-2H-[1]-benzothiopyran-3-amine, 12.9 g of sodium carbonate monohydrate, 21 mL of n-propyl-iodide in 40 mL of toluene and 40 mL of water is refluxed with stirring for 3 days. The organic layer is dried and the solvent removed in vacuo. The residue is dissolved in ether and acidified with ethanolic hydrochloric acid to afford 3,4-dihydro-N,N-dipropyl-5-methoxy-2H-[1]-benzothiopyran-3-amine hydrochloride melting at 219°–221°.

The starting material is prepared as follows:

To a cooled mixture of 30.6 g of m-methoxybenzenethiol, 54.4 g of 45% potassium hydroxide in 100 mL of dimethylsulfoxide is added 36.0 g of alpha(bromomethyl)acrylic acid in 25 mL of dimethylsulfoxide at such a rate as to maintain the reaction temperature at 50°–55°. After 1 hour the reaction mixture is diluted with water and washed with ether. After acidification, the product is extracted with ether, the organic layer is dried over magnesium sulfate and the solvent is removed in vacuo to afford alpha-(3-methoxybenzenethiomethyl)acrylic acid. This material is dissolved in 570 mL of o-dichlorobenzene and 7.2 g of triethylamine and heated to 200° for 5 hours. After cooling, the products are extracted with sodium bicarbonate solution, the aqueous layer is acidified and the products extracted with ether. After drying over magnesium sulfate, the solvent is removed in vacuo to afford a mixture of 3,4-dihydro-5-methoxy-2H-[1]-benzothiopyran-3-carboxylic acid and 3,4-dihydro-7-methoxy-2H-[1]-benzothiopyran-3-carboxylic acid.

This mixture of acids is dissolved in 500 mL of t-butyl alcohol and treated with 17 g of triethylamine and 36 mL of diphenylphosphoryl azide. After 5 hr. reflux, the solvent is removed in vacuo and the residue is dissolved in ether and washed with 1N sodium hydroxide and 1N hydrochloric acid. After drying over magnesium sulfate, the solvent is removed in vacuo and the residue is chromatographed on silica gel (1 kg) with ether/hexane (1:4) as the eluent to afford in succession N-t-butoxycarbonyl-3,4-dihydro-5-methoxy-2H-[1]-benzothiopyran-3-amine and N-t-butoxycarbonyl-3,4-dihydro-7-methoxy-2H-[1]-benzothiopyran-3-amine.

A solution of 10 g of N-t-butoxycarbonyl-3,4-dihydro-5-methoxy-2H-[1]-benzothiopyran-3-amine in 30 mL of trifluoroacetic acid is kept at room temperature for 1 hr. The solvent is removed in vacuo, the residue is treated with 1N NaOH and the product is extracted with ether. After drying over magnesium sulfate, the solvent is removed in vacuo to afford 3,4-dihydro-5-methoxy-2H-[1]-benzothiopyran-3-amine as an oil.

Similarly prepared are:
(B) 3,4-Dihydro-N,N-dimethyl-8-methoxy-2H-[1]-benzothiopyran-3-amine hydrochloride, m.p. 200°–204°.
(C) 3,4-Dihydro-N,N-dipropyl-8-methoxy-2H-[1]-benzothiopyran-3-amine hydrochloride, m.p. 171°–174°.
(D) 3,4-Dihydro-N,N-dipropyl-6-fluoro-2H-[1]-benzothiopyran-3-amine hydrochloride, m.p. 199°–201.5°.

(E) 3,4-Dihydro-N,N-dipropyl-8-fluoro-2H-[1]-benzothiopyran-3-amine hydrochloride, m.p. 208°–211°.

EXAMPLE 2

(A) To a solution of 2.9 mL of diphenylphosphine and 7.4 mL of 2.2M n-butyllithium in 17 mL of dry tetrahydrofuran is added 2.5 g of N,N-dipropyl-5-methoxy-3,4-dihydro-2H-[1]-benzothiopyran-3-amine. After refluxing for 2 hr, the reaction mixture is neutralized, diluted with ether and washed with water. After drying over magnesium sulfate, the solvent is removed in vacuo, the residue is dissolved in ether and acidified with ethanolic hydrochloric acid to afford 3,4-dihydro-N,N-dipropyl-5-hydroxy-2H-[1]-benzothiopyran-3-amine hydrochloride, m.p. 223°–226°.

Similarly prepared are:
(B) 3,4-Dihydro-N,N-dipropyl-6-hydroxy-2H-[1]-benzothiopyran-3-amine hydrochloride, m.p. 145°–150°.
(C) 3,4-Dihydro-N,N-dipropyl-7-hydroxy-2H-[1]-benzothiopyran-3-amine hydrochloride, m.p. 202°–205°.
(D) 3,4-Dihydro-N,N-dipropyl-8-hydroxy-2H-[1]-benzothiopyran-3-amine benzoate, m.p. 144°–146.5°.
(E) 3,4-Dihydro-N,N-dipropyl-7-propyl-8-hydroxy-2H-[1]-benzothiopyran-3-amine fumarate, m.p. 94°–96°.

EXAMPLE 3

(A) A mixture of 1.0 g of 3,4-dihydro-2H-[1]-benzothiopyran-3-one, J. Org. Chem. 34, 1566 (1969), 2 mL of N,N-dipropylamine, 25 mL of toluene and 0.1 mL of trifluoroacetic acid is refluxed in a Dean-Stark apparatus for 16 hr. The solvent is removed in vacuo and the residue is added to a solution of 1 g of sodium cyanoborohydride in 20 mL of ethanol and 4 mL of acetic acid. After 1 hr. at room temperature, the reaction mixture is diluted with 6N hydrochloric acid, washed with ether, made basic with 45% potassium hydroxide and reextracted with ether. After drying over magnesium sulfate, the solvent is removed in vacuo. Addition of ethanolic hydrochloric acid to an ether solution of the resulting residue affords 3,4-dihydro-N,N-dipropyl-2H-[1]-benzothiopyran-3-amine hydrochloride melting at 147°–150°.

Similarly prepared are:
(B) 3,4-Dihydro-N,N-dimethyl-2H-[1]-benzothiopyran-3-amine hydrochloride, m.p. 175°–180°.
(C) 3,4-Dihydro-8-methoxy-N,N-dipropyl-2H-[1]-benzothiopyran-3-amine hydrochloride, m.p. 171°–174.5°.

The starting material is prepared as follows:
To a mixture of 28 g of o-methoxybenzenethiol, 50 g of 45% potassium hydroxide in 70 ml of dimethyl sulfoxide is added 33 g of α-(bromethyl)-acrylic acid in 30 ml of dimethyl sulfoxide while maintaining the temperature at 50°–60°. After 1 hour the reaction mixture is poured onto dilute hydrochloric acid and the products are extracted with ether. The ether layer is extracted with sodium bicarbonate solution. Acidification of the aqueous bicarbonate extracts affords α-(o-methoxyphenylthiomethyl)-acrylic acid, m.p. 101°–104°.

A mixture of 22.5 g of α-(o-methoxyphenylthiomethyl)-acrylic acid, 2.53 g of triethylamine and 200 ml o-dichlorobenzene is heated for 12 hours at 195°. After dilution with ether the products are extracted with sodium bicarbonate solution. Acidification of the basic extracts affords 8-methoxy-3,4-dihydro-2H-[1]-benzothiopyran-3-carboxylic acid, m.p. 223°–226°.

To a solution of 10 g of 8-methoxy-3,4-dihydro-2H-[1]-benzothiopyran-3-carboxylic acid in 200 ml of methylene chloride is added 6.2 g of N-chlorosuccinimide in portions. After 10 minutes 60 g of silica gel is added. The reaction mixture is stirred for 15 minutes, filtered through 40 g of silica gel eluting with ether/methylene chloride (1:1). The solvent is concentrated to 100 ml, 5 ml of triethylamine and 5 g of ethyl chloroformate are added. After concentration 5 g of sodium azide in 60 ml of dimethylformamide are added and the reaction mixture is stirred for 1 hour. After dilution with water the products are extracted with ether, the ether extract is dried and evaporated to dryness; 150 ml of 10% aqueous sulfuric acid is added and the reaction mixture is heated under reflux for 2 hours. The reaction mixture is extracted with ether, the ether extract is washed with dilute sodium bicarbonate solution, dried and evaporated to dryness. Crystallization from methanol affords 8-methoxy-3,4-dihydro-2H-[1]-benzothiopyran-3-one, m.p. 60°.

(D) 3,4-dihydro-5-methoxy-N,N-dipropyl-2H-[1]-benzothiopyran-3-amine hydrochloride, m.p. 219°–221°.

The starting material, 3,4-dihydro-5-methoxy-2H-[1]-benzothiopyran-3-one can be prepared as described above from 3,4-dihydro-5-methoxy-2H-[1]-benzothiopyran-3-carboxylic acid (example 1).

EXAMPLE 4

(A) To a solution of 220 mg of 3,4-dihydro-N,N-dipropyl-5-hydroxy-2H-[1]-benzothiopyran in 2 mL or dimethyl sulfoxide is added 100 mg of 50% sodium hydride and 150 mg of ethyl iodide. After 1 hr at 50°, the reaction is diluted with water and the product extracted with ether. After drying over magnesium sulfate, the solvent is removed in vacuo and the residue is acidified with ethanolic hydrocholoric acid. Dilution with ether affords 3,4-dihydro-N,N-dipropyl-5-ethoxy-2H-[1]-benzothiopyran-3-amine hydrochloride melting at 168°–174°. After recrystallization from water melting point is 174°–175°.

Similarly prepared are:
(B) 3,4-Dihydro-N,N-dipropyl-5-propyloxy-2H-[1]-benzothiopyran-3-amine hydrochloride, m.p. 156°–161°.
(C) 3,4-Dihydro-N,N-dipropyl-5-benzyloxy-2H-[1]-benzothiopyran-3-amine hydrochloride.

EXAMPLE 5

(A) A mixture of 500 mg of 3,4-dihydro-5-methoxy-2H-[1]-benzothiopyran-3-amine and 361 mg of acetic anhydride in 10 mL of methylene chloride is kept at room temperature for 15 min. The solvent is removed in vacuo and the resulting 3,4-dihydro-N-acetyl-5-methoxy-2H-[1]-benzopyran-3-amine is dissolved in 10 mL of 1M diborane in tetrahydrofuran. After 3 hr reflux, the reaction mixture is poured into 6N hydrochloric acid, washed with ether, basified with 45% potassium hydroxide and reextracted with ether. After drying over magnesium sulfate, the solvent is removed in vacuo. Acidification with ethanolic hydrochloric acid affords 3,4-dihydro-N-ethyl-5-methoxy-2H-[1]-benzothio-pyran-3-amine hydrochloride melting at 222°–224°.

(B) Similarly prepared is 3,4-dihydro-N-ethyl-5-methoxy-7-methyl-2H-[1]-benzothiopyran-3-amine hydrochloride, melting at 250°–252°.

EXAMPLE 6

To a solution of 5 g of 8-methoxy-3,4-dihydro-2H-[1]-benzothiopyran-3-one (J. Chem. Soc. 1948, 1610), and 4 g of anhydrous dimethylamine in 50 ml of toluene is stirred with 4 A molecular sieves for 2 hours. The reaction mixture is filtered and the solvent removed in vacuo. This residue is added to a solution of 3.2 g of sodium cyanoborohydride in 10 ml of acetic acid and 50 ml of ethanol. After 30 minutes at room temperature, the reaction mixture is poured onto 3N hydrochloric acid, and washed with ether. After basification of the aqueous layer followed by ether extraction, the organic layer is dried over magnesium sulfate and the solvent removed in vacuo. The residue is added to a solution of lithium diphenylphosphide prepared from 4.9 g diphenylphosphine, 19 ml of 1.3M butyl lithium in hexane and 70 ml of dry tetrahydrofuran, and the mixture is refluxed for 1 hour. The reaction mixture is poured onto 2N hydrochloric acid and washed with ether. After neutralization of the aqueous layer with sodium bicarbonate, the product is extracted with ether and the solvent is removed in vacuo after drying over magnesium sulfate. The residue is dissolved in ethanol; after acidification with 5.4N ethanolic hydrogen chloride and cooling, 8-hydroxy-3,4-dihydro-N,N-dimethyl-2H-[1]-benzothiopyran-3-amine hydrochloride, melting point 172°–173°, is obtained.

EXAMPLE 7

A mixture of 4.0 g of 8-methoxy-3,4-dihydro-2H-[1]-benzopyran-3-one (J. Chem. Soc. 1948, 1610), 6 ml of dipropylamine, 0.2 ml of trifluoroacetic acid and 30 ml of toluene is refluxed for 1.5 hours in a Dean-Stark apparatus. The solvent is removed in vacuo and the residue dissolved in a small volume of ethanol. This mixture is added to a mixture of 2 g of sodium cyanoborohydride, 5 ml of acetic acid and 25 ml of ethanol. After stirring for 15 minutes at room temperature, the reaction mixture is poured onto 3N aqueous hydrochloric acid and washed with ether. The aqueous phase is made basic with 50% aqueous potassium hydroxide and the product is extracted with ether. After dring over magnesium sulfate, the solvent is removed. The residue is dissolved in ethanol, the solution is acidified with 5.6M ethanolic hydrogen chloride, and ether and ethyl acetate are added. Cooling leads to crystallization of 8-methoxy-3,4-dihydro-N,N-dipropyl-2H-[1]-benzopyran-3-amine hydrochloride, melting at 150°–152°.

EXAMPLE 8

To a solution of 2.8 ml of diphenyl phosphine in 25 ml of dry tetrahydrofuran is added 10 ml of 1.6 M butyllithium in hexane at 0°. To the resulting solution is added 2.5 g of 8-methoxy-3,4-dihydro-N,N-dipropyl-2H-[1]-benzopyran-3-amine and the resulting mixture is refluxed for 10 minutes. The reaction mixture is poured onto water, diluted with ether and hexane and the product is extracted with 3N hydrochloric acid. The aqueous layer is washed with ether, neutralized with sodium bicarbonate and the product extracted with ethyl acetate. After drying over magnesium sulfate, the solvent is removed and the residue dissolved in ethanol. After acidification with 5.6M ethanolic hydrogen chloride and dilution with ethyl acetate and ether, the mixture is cooled to 0° to crystallize 8-hydroxy-3,4-dihydro-N,N-dipropyl-2H-[1]-benzopyran-3-amine hydrochloride, melting at 174°–5°.

EXAMPLE 9

A mixture of 6.4 g of 5-methoxy-3,4-dihydro-2H-[1]-benzopyran-3-one, 30 ml of dipropylamine, 0.5 ml of trifluoroacetic acid and 200 ml of toluene is refluxed in a Dean-Stark apparatus for 3 hours. The solution concentrated in vacuo and the residue is added to a solution of 7 g of sodium cyanoborohydride in 160 ml of ethanol and 40 ml of acetic acid. After 15 minutes at room temperature most of the solvent is removed in vacuo. The residue is dissolved in 6N hydrochloric acid and washed with ether. The aqueous layer is made basic and the product is extracted with ether. The aqueous layer is made basic and the product is extracted with ether. The ether layer is dried over magnesium sulfate and the solvent is removed in vacuo, to afford 5-methoxy-3,4-dihydro-N,N-dipropyl-2H-[1]-benzopyran-3-amine which is treated with ethanolic hydrochloric acid to afford 5-methoxy-3,4-di-hydro-N,N-dipropyl-2H-[1]-benzopyran-3-amine hydrochloride, m.p. 219°–221°.

The starting material is prepared as follows:

To a well stirred solution of 36.4 g of 5-methoxy-2H-[1]-benzopyran in 300 ml of acetone and 100 ml of water is added 29 g of N-bromosuccinimide in portions over 5 minutes. After 4 hours at room temperature the reaction mixture is diluted with water and the product is extracted with ether. After washing the combined ether fraction with water, it is dried over magnesium sulfate and the solvent is removed in vacuo. The crystalline residue is triturated with ether/hexane to afford trans-3-bromo-4-hydroxy-5-methoxy-3,4-dihydro-2H-[1]-benzopyran.

To a suspension of 5.0 g sodium hydride in 100 ml of dry tetrahydrofuran is added with stirring a solution of 13 g of trans-3-bromo-4-hydroxy-5-methoxy-3,4-dihydro-2H-[1]-benzopyran in 150 ml of dry tetrahydrofuran in a dropwise fashion. After 30 minutes stirring at room temperature, the reaction mixture is filtered through filter-cel and the solvent is removed in vacuo. The residue is dissolved in 150 ml of toluene, 1.0 g of anhydrous zinc iodide is added and the mixture is refluxed for 15 minutes. The reaction mixture is filtered through 120 g of silica gel with methylene chloride as the eluent to afford 5-methoxy-3,4-dihydro-2H-[1]-benzopyran-3-one (5-methoxychroman-3-one) as an oil.

EXAMPLE 10

To a solution of 8.55 ml of diphenylphosphine in 50 ml of dry tetrahydrofuran is added 22 ml of 2.2M n-butyl lithium in hexane at 0°. To the resulting solution is added 7.3 g of 5-methoxy-3,4-dihydro-N,N-dipropyl-2H-[1]-benzopyran-3-amine dissolved in a small quantity of tetrahydrofuran, and the reaction mixture is refluxed for 4 hours. The reaction mixture is diluted with ether and the product extracted with 3 N hydrochloric acid. After washing the aqueous layer with ether, it is neutralized with sodium bicarbonate and the product is extracted with methylene chloride. After drying over magnesium sulfate the solvent is removed in vacuo, and the residue is dissolved in an acetonitrile/ether mixture. After acidification with 3N ethanolic hydrogen chloride 5-hydroxy-3,4-dihydro-N,N-dipropyl-2H-[1]-benzopyran-3-amine hydrochloride, melting at 206°–210° is obtained.

EXAMPLE 11

(A) To a suspension containing 55 mg of sodium hydride in 10 ml of dimethyl sulfoxide is added 290 mg of 5-hydroxy-N,N-dipropyl-3,4-dihydro-2H-[1]-benzopyran-3-amine. After 15 minutes at room temperature 180 mg of ethyl iodide is added and the reaction is stirred for 3 hours at room temperature. The solvent is removed in vacuo and the reaction is diluted with water. The product is extracted with ether and the organic layer is dried over magnesium sulfate and the solvent is removed in vacuo. The residue is taken up in ether and acidified with 6N ethanolic hydrogen chloride to afford 5-ethoxy-N,N-dipropyl-3,4-dihydro-2H-[1]-benzopyran-3-amine hydrochloride melting at 135°–137°.

Similarly prepared are:
(B) 5-propyloxy-N,N-dipropyl-3,4-dihydro-2H-[1]-benzopyran-3-amine hydrochloride melting at 127°–128°.
(C) 5-ethoxy-N,N-diethyl-3,4-dihydro-2H-[1]-benzopyran-3-amine hydrochloride;
(D) 5-benzyloxy-N,N-dipropyl-3,4-dihydro-2H-[1]-benzopyran-3-amine hydrochloride.

EXAMPLE 12

(A) To a solution of 2.86 g of 5-hydroxy-3,4-dihydro-N,N-dipropyl-2H-[1]-benzopyran-3-amine hydrocholoride in 40 ml of methylene chloride is added 3.9 g of diisopropylethylamine and 1.6 g of pivaloyl chloride, and the mixture is stirred for 16 hours. After dilution with methylene chloride, the reaction mixture is washed with water and saturated sodium bicarbonate solution, dried over magnesium sulfate, and the solvent is removed in vacuo. Addition of sufficient isopropanolic hydrogen bromide precipitates 5-trimethylacetoxy-3,4-dihydro-N,N-dipropyl-2H-[1]-benzopyran-3-amine hydrobromide, melting point 130°–139°.

Similarly prepared are:
(B) 8-trimethylacetoxy-3,4-dihydro-N,N-dipropyl-2H-[1]-benzopyran-3-amine hydrochloride, melting at 195°–196°;
(C) 5-acetoxy-3,4-dihydro-N,N-dipropyl-2H-[1]-benzopyran-3-amine;
(D) 5-dimethylcarbamoyloxy-3,4-dihydro-N,N-dipropyl-2H-[1]-benzopyran-3-amine;
(E) 5-benzoyloxy-3,4-dihydro-N,N-dipropyl-2H-[1]-benzopyran-3-amine;
(F) 8-benzoyloxy-3,4-dihydro-N,N-dipropyl-2H-[1]-benzothiopyran-3-amine;
(G) 5-trimethylacetoxy-3,4-dihydro-N,N-dipropyl-2H-[1]-benzothiopyran-3-amine;
(H) 5-dimethylcarbamoyloxy-3,4-dihydro-N,N-dipropyl-2H-[1]-benzothiopyran-3-amine.

EXAMPLE 13

To a solution of 5-ethoxy-3,4-dihydro-2H-[1]-benzothiopyran-3-one (100 g) in toluene (900 mL) is added di-n-propylamine (97.5 g, 132 mL) and dichloroacetic acid (220 mg). The solution is refluxed and the water that is formed is collected in a Dean-Stark trap. After refluxing overnight the solvent is stripped to obtain an oil which NMR indicates to be a mixture of the enamine double bond isomers N,N-dipropyl-5-ethoxy-2H-[1]-benzothiopyran-3-amine and N,N-dipropyl-5-ethoxy-4H-[1]-benzothiopyran-3-amine. The crude material is used in the reduction as is.

To a solution of the enamine mixture (137 g) in tetrahydrofuran (308 mL) is added a solution of sodium cyanoborohydride (32.6 g) in tetrahydrofuran (308 mL). The combined solution is cooled to 5° and to this is added acetic acid (308 mL) dropwise keeping the temperature below 5°. After the addition is complete the mixture is allowed to stand overnight at room temperature and the solvent is stripped in vacuo to give a residue which is dissolved in a mixture of ether (500 mL) and water (500 mL), and the mixture is then basified with concentrated ammonium hydroxide. The aqueous phase is washed with more ethyl ether (50 mL). The combined organic phases are washed with hydrochloric acid (6N, 240 mL) and the acidic washes are then backwashed with ethyl ether which is discarded. The acidic solution is made basic with concentrated ammonium hydroxide and then extracted with ethyl ether (2×250 mL). The combined organic extracts are washed with water, dried over anhydrous magnesium sulfate, filtered and the filtrate is evaporated in vacuo togive a dark oil.

On distillation of the crude amine there is obtained an amber oil, bp 160°–165°/0.6 mm; the purified amine is dissolved in ethyl ether and into this solution is passed hydrogen chloride gas until the solution is somewhat acidic. The salt slowly crystalizes. The resulting salt is recrystallized from water (50 mL) to obtain 3,4-dihydro-N,N-dipropyl-5-ethoxy-2H-[1]-benzothiopyran-3-amine hydrochloride, m.p. 174°–175°.

The starting material is prepared as follows:
A slurry of ethyl α-(2,6-dioxocyclohexyl)acetate hydrate (1.53 kg) in methylene chloride (7.7L) is brought to reflux and then thionyl chloride (1.80 kg) is added dropwise over a period of 1.75 hours. The solution is refluxed for 3 hours and then evaporated in vacuo to yield an oil which is distilled to give ethyl α-(2-chloro-6-oxocyclohex-1-enyl)acetate as a yellow oil, bp 115°–125°/0.2 mm.

To a solution of α-(2-chloro-6-oxocyclohex-1-enyl)acetate (700 g) in anhydrous ethanol (2.1L) is added ethyl mercaptoacetate (410 g). Then to this solution is added at 5° a solution of potassium t-butoxide (381 g) in anhydrous ethanol (1.8L) dropwise over a period of 1.5 hours. This is stirred for an additional 2 hours at this temperature and then kept at room temperature overnight. The solvent is removed in vacuo and the residue is mixed with ethyl ether (3L) and water. The layers are separated and the organic layer is washed with water (2×400 mL), dried over anhydrous magnesium sulfate, filtered and the filtrate is evaporated in vacuo to yield ethyl α-(2-ethoxy-carbonylmethylthio-6-oxocyclohex-1-enyl)acetate as a light yellow oil.

To a solution of α-(2-ethoxycarbonylmethylthio-6-oxocyclohex-1-enyl)acetate (156 g) in acetic acid (500 mL) is added acetic anhydride (750 mL). The solution is heated to 100° and a solution of sulfuric acid (53 g) in acetic acid (250 mL) is added dropwise. After addition is completed, the solution is heated until gas evolution ceases and the solvent is then removed in high vacuo to yield an oil which is mixed with ether and water. The layers are separated and the organic layer is washed with water, saturated sodium bicarbonate until neutral and then again water. The organic layer is then dried over anhydrous magnesium sulfate, filtered and evaporated in vacuo to yield ethyl 6-acetoxy-2-(ethoxycarbonylmethylthio)-phenylacetate as an oil.

Ethyl 6-acetoxy-2-(ethoxycarbonylmethylthio)-phenylacetate (132 g) is added at room temperature to a solution of ammonia (34 g) in anhydrous ethanol (1.0L). After standing for 2 hours the solvent is evaporated in vacuo and the residue is mixed with methylene chloride and 1N hydrochloric acid. The layers are separated and the organic layer is washed with water to neutrality, dried over anhydrous magnesium sulfate, filtered and the filtrate is evaporated in vacuo to obtain (as shown by NMR) ethyl 6-hydroxy-2-(ethoxycarbonylmethylthio)-phenylacetate as an oil.

To a solution of ethyl 6-hydroxy-2-(ethoxycarbonylmethylthio)-phenylacetate (20.0 g) in anhydrous ethanol (200 mL) is added diethyl sulfate (10.3 g). To this is added in portions solid potassium t-butoxide (7.52 g), keeping the temperature below 30° with a cold-water bath. After stirring overnight at room temperature, the solvent is removed in vacuo and the residue is mixed with ether and water. The layers are separated and the organic layer is washed with ice-cold sodium hydroxide (0.5N, 40 mL) to remove starting material. The ether layer is washed with water to neutrality, dried over anhydrous magnesium sulfate, filtered and the filtrate is evaporated in vacuo to give (as shown by NMR) ethyl 6-ethoxy-2-(ethoxycarbonylmethylthio)-phenylacetate as an oil.

To a solution of ethyl 6-ethoxy-2-(ethoxycarbonylmethylthio)-phenylacetate (17.8 g) in ethanol (112 mL) is added a solution of potassium hydroxide (85%, 7.21 g) in water (28 mL). The solution is refluxed for 2 hours, is concentrated in vacuo to remove the ethanol, and is diluted with water (200 mL). Hydrochloric acid (12N, 10.0 mL) is added. The product which originally precipitates as an oil slowly crystallizes. After crystallization is complete the solid is filtered off, air-dried for 2 hours and then dried in vacuo at 50° to obtain 6-ethoxy-2-(carboxymethylthio)phenylacetic acid, m.p. 147°–150°.

To a suspension of the diacid (12.4 g) in acetic anhydride (115 mL) is added anhydrous sodium acetate (10.6 g). This mixture is brought to reflux (gas evolution) and kept at this temperature for 20 minutes. The solution is evaporated and the residue is mixed with ether and aqueous sodium carbonate. Enough carbonate solution is used until the solution remains basic. The layers are separated and the organic layer is washed with more carbonate solution and then water till neutrality is reached. The ether extracts are then dried over anhydrous magnesium sulfate, filtered and the filtrate is evaporated in vacuo to obtain an oil which is distilled to obtain 3-acetoxy-5-ethoxy-2H-[1]-benzothiopyran, b.p. 155°–163°/0.25 mm.

To a solution of the enol acetate (16.3 g) in ethanol (147 mL) is added a solution of hydrochloric acid (12N, 1.49 mL) diluted with water (16.4 mL). This solution is refluxed for 6 hours and concentrated in vacuo to remove the ethanol. The aqueous residue is then extracted with ether. The organic extract is washed with saturated sodium bicarbonate solution until the extract remains basic, then with water, dried over anhydrous magnesium sulfate, filtered, and the filtrate is evaporated in vacuo to yield, as indicated by NMR, 5-ethoxy-3,4-dihydro-2H-[1]-benzothiopyran-3-one as an oil.

EXAMPLE 14

(A) Preparation of 10,000 tablets each containing 20 mg of the active ingredient:
Formula:

| | |
|---|---|
| 3,4-Dihydro-N,N—dipropyl-5-ethoxy-2H—[1]-benzothiopyran-3-amine hydrochloride | 200.00 g |
| Lactose | 2,400.00 g |
| Corn starch | 125.00 g |
| Polyethylene glycol 6,000 | 150.00 g |
| Magnesium stearate | 40.00 g |
| Purified water | q.s |

Procedure:

All the powders are passed through a screen with openings of 0.6 mm. Then the drug substance, lactose, magnesium stearate and half of the starch are mixed in a suitable mixer. The other half of the starch is suspended in 65ml of water and the suspension added to the boiling solution of the polyethylene glycol in 260 ml of water. The paste formed is added to the powders, which are granulated, if necessary, with an additional amount of water. The granulate is dried overnight at 35°, broken on a screen with 1.2 mm openings and compressed into tablets, using concave punches uppers bisected.

(B) Preparation of 1,000 capsules each containing 10 mg of the active ingredient:
Formula

| | |
|---|---|
| 3,4-Dihydro-N,N—dipropyl-5-ethoxy-2H—[1]-benzothiopyran-3-amine hydrochloride | 10.0 g |
| Lactose | 207.0 g |
| Modified starch | 80.0 g |
| Magnesium stearate | 3.0 g |

Procedure:

All the powders are passed through a screen with openings of 0.6 mm. Then the drug substance is placed in a suitable mixer and mixed first with the magnesium stearate, then with the lactose and starch until homogeneous. No. 2 hard gelatin capsules are filled with 300 mg of said mixture each, using a capsule filling machine.

(C) Preparation of 1,000 capsules each containing 25 mg of the active ingredient:
Formula:

| | |
|---|---|
| 5-Hydroxy-3,4-dihydro-N,N—dipropyl-2H—[1]-benzopyran-3-amine hydrochloride | 25.0 g |
| Lactose | 192.0 g |
| Modified starch | 80.0 g |
| Magnesium stearate | 3.0 g |

Procedure:

All the powders are passed through a screen with openings of 0.6 mm. Then the drug substance is placed in a suitable mixer and mixed first with the magnesium stearate, then with the lactose and starch until homogeneous. No. 2 hard gelatin capsules are filled with 300 mg of said mixture each, using a capsule filling machine.

EXAMPLE 15

To a solution of 9.1 ml of diphenylphosphine in 60 ml of dry tetrahydrofuran is added 33 ml of 1.6M n-butyl lithium in hexane at 0°. To the resulting solution is added 8.0 g of 6-methoxy-3,4-dihydro-N,N-dipropyl-2H-[1]-benzopyran-3-amine dissolved in a small quantity of tetrahydrofuran, and the reaction mixture is refluxed for 4 hours. The reaction mixture is diluted with ether and the product extracted with 3N hydrochloric acid. After washing the aqueous layer with ether, it is neutralized with sodium bicarbonate and the product is extracted with methylene chloride. After drying over magnesium sulfate the solvent is removed in vacuo, and the residue is dissolved in an acetonitrile/ether mixture. After acidification with 3N ethanolic hydrogen chloride 6-hydroxy-3,4-dihydro-N,N-dipropyl-2H-[1]-benzopyran-3-amine hydrochloride, melting at 188°–190.5° is obtained.

The starting material is prepared as follows:

To a well stirred solution of 60 g of 6-methoxy-2H-[1]-benzopyran, J. Org. Chem. 38, 3832 (1973), in 300 ml of acetone and 150 ml of water is added 70 g of N-bromosuccinimide in portions over 5 minutes. After 10 minutes at room temperature the reaction mixture is diluted with water and the product is extracted with ether. After washing the combined ether fraction with water, it is dried over magnesium sulfate and the solvent is removed in vacuo. The crystalline residue is triturated with ether/hexane to afford trans-3-bromo-4-hydroxy-6-methoxy-3,4-dihydro-2H-[1]-benzopyran melting at 98°-99°.

To a suspension of 2.0 g oodium hydride in 100 ml of dry tetrahydrofuran is added with stirring a solution of 20 g of trans-3-bromo-4-hydroxy-6-methoxy-3,4-dihydro-2H-[1]-benzopyran in 200 ml of dry tetrahydrofuran in a dropwise fashion. After 30 minutes stirring at room temperature, the reaction mixture is filtered through filter-cel and the solvent is removed in vacuo. The residue is dissolved in 100 ml of toluene, 1.0 g of anhydrous zinc iodide is added and the mixture is heated at 80° C. for 1 hour. The reaction mixture is filtered through 120 g of silica gel with methylene chloride as the eluent to afford after recrystallization from ether 6-methoxy-3,4-dihydro-2H-[1]-benzopyran-3-one (6-methoxy-chroman-3-one), melting at 67°-72°.

A mixture of 11.58 g of 6-methoxy-3,4-dihydro-2H-[1]-benzopyran-3-one, 26 g of dipropylamine, 0.3 ml of trifluoroacetic acid and 160 ml of toluene is refluxed in a Dean-Stark apparatus for 2 hours. The solution concentrated in vacuo and the residue is added to a solution of 8 g of sodium cyanoborohydride in 160 ml of ethanol and 40 ml of acetic acid. After 15 minutes at room temperature most of the solvent is removed in vacuo. The residue is dissolved in 6N hydrochloric acid and washed with ether. The aqueous layer is made basic and the product is extracted with ether. The aqueous layer is made basic and the product is extracted with ether. The ether layer is dried over magnesium sulfate and the solvent is removed in vacuo, to afford 6-methoxy-3,4-dihydro-N,N-di-propyl-2H-[1]-benzopyran-3-amine. The fumaric acid salt melts at 107°-113°.

EXAMPLE 16

Compounds prepared by methods analogous to those described in the previous examples:
(a) 6,7-Dihydroxy-3,4-dihydro-N,N-dipropyl-2H-[1]-benzopyran-3-amine hydrochloride, melting point 187°-191°.

The starting material 6,7-dimethoxy-3,4-dihydro-2H-[1]-benzopyran-3-one, J. Am. chem. Soc. 87, 3958 (1965), is prepared as follows.

A well stirred mixture of 81.7 g of 2-hydroxy-4,5-dimethoxybenzaldehyde, 62 g of potassium carbonate, 100 ml of t-butyl acrylate and 320 ml of dimethyl formamide is heated at 140° for 5 hours. Most of the solvent is removed, the reaction mixture is diluted with water and the product is extracted with ethyl acetate/ether. After washing with 1N aqueous sodium hydroxide solution and drying over magnesium sulfate, the solvent is removed and the residue dissolved in 130 ml of trifluoroacetic acid. After 10 minutes, the solid mass is diluted with ice water and 70 ml of 20% aqueous sodium hydroxide solution. The precipitated product is collected by filtration and air-dried to yield 6,7-dimethoxy-2H-[1]-benzopyran-3-carboxylic acid, melting at 225°-228°.

To a solution of 74.4 g of the acid and 56 ml of triethylamine in 325 ml of methylene chloride is added 33 ml of ethyl chloroformate in a dropwise fashion at 0°. After 30 minutes at 0° the solvent is removed in vacuo and replaced with 400 ml of dimethylformamide. Sodium azide (33 g) is added and the mixture stirred for 16 hours at room temperature. After dilution with water the precipitated product is collected and washed with water. This material is refluxed in 500 ml of ethanol for 3 hours after which time the solvent is removed; to the residue is added 500 ml of 10% sulfuric acid. The reaction mixture is refluxed with vigorous stirring for 4 hours. After cooling the product is extracted with ether, the ether layer is washed with water and saturated sodium bicarbonate solution, and the solvent is removed after drying over magnesium sulfate. Crystallization from ethyl acetate/ether yields 6,7-dimethoxy-3,4-dihydro-2H-[1]-benzopyran-3-one, melting at 126°-129.5°.

(b) 7-Hydroxy-3,4-dihydro-N,N-dipropyl-2H-[1]-benzopyran-3-amine hydrochloride, melting point 168°-170°.

The 7-methoxy-2H-[1]-benzopyran-3-carboxylic acid starting material, melting point 196°-204°, is converted to the 7-methoxy-3,4-dihydro-2H-[1]-benzopyran-3-one intermediate as described under (a) above.

(c) 6-Hydroxy-3,4-dihydro-N,N-dimethyl-2H-[1]-benzopyran-3-amine, melting point 199°-203°.

(d) 6,7-Dihydroxy-3,4-dihydro-N,N-dimethyl-2H-[1]-benzopyran-3-amine hydrochloride, melting point 236°-237°.

(e) 6-Hydroxy-3,4-dihydro-N,N-dibutyl-2H-[1]-benzopyran-3-amine hydrochloride.

(f) 6-trimethylacetoxy-3,4-dihydro-N,N-dipropyl-2H-[1]-benzopyran-3-amine hydrochloride, melting at 205°-213°.

(g) 6-acetoxy-3,4-dihydro-N,N-dipropyl-2H-[1]-benzopyran-3-amine.

(h) 6-dimethylcarbamoyloxy-3,4-dihydro-N,N-dipropyl-2H-[1]-benzopyran-3-amine.

(i) 6-benzoyloxy-3,4-dihydro-N,N-dipropyl-2H-[1]-benzopyran-3-amine.

EXAMPLE 17

(a) A mixture of 5.5 g of 5-methoxy-N,N-dipropyl-3,4-dihydro-2H-[1]-benzopyran-3-amine and 3.9 g of dibenzoyl-D-tartaric acid in 65 ml of methyl ethyl ketone is heated and cooled to room temperature. The resulting solid is collected and recrystallized three times from methyl ethyl ketone. Conversion to the free base yields the levoratory (−)-5-methoxy-N,N-dipropyl-3,4-dihydro-2H-[1]-benzopyran-3-amine, $[\alpha]_D^{25} = -74.79°$. This is in turn converted to (−)-5-methoxy-N,N-dipropyl-3,4-dihydro-2H-[1]-benzopyran-3-amine hydrochloride, $[\alpha]_D = -21.79°$ (methanol), m.p. 144°-146°.

(b) using dibenzoyl-L-tartaric acid, dextrorotatory (+)-5-methoxy-N,N-dipropyl-3,4-dihydro-2H-[1]-benzopyran-3-amine hydrochloride, $[\alpha]_D = +19.59°$ (methanol), m.p. 144°-146°, the more active enantiomer is obtained.

EXAMPLE 18

(a) using procedure previously described (Example 10), (−)-5-methoxy-N,N-dipropyl-3,4-dihydro-2H-[1]-benzopyran-3-amine is converted to (−)-5-hydroxy-N,N-dipropyl-3,4-dihydro-2H-[1]-benzopyran-3-amine hydrochloride, $[\alpha]_D = -24.84°$ (methanol), m.p. 224°-227°.

(b) Similarly, the more active dextrorotatory enantiomer (+)-5-hydroxy-N,N-dipropyl-3,4-dihydro-2H-[1]- benzopyran-3-amine hydrochloride $[\alpha]_D = +23.27°$ (methanol), m.p. 225°–228°, is obtained.

EXAMPLE 19

(a) Using procedure previously described (Example 11), (−)-5-hydroxy-N,N-dipropyl-3,4-dihydro-2H-[1]-benzo-pyran-3-amine is converted to (−)-5-ethoxy-N,N-dipropyl-3,4-dihydro-2H-[1]benzopyran-3-amine hydrochloride, $[\alpha]_D = -32.88°$ (methanol), m.p. 149°–150°.

(b) Similarly, the more active dextrorotatory enantiomer (+)-5-ethoxy-N,N-dipropyl-3,4-dihydro-2H-[1]-benzopyran-3-amine hydrochloride, $[\alpha]_D = +31.91°$ (methanol), m.p. 148°–149°, is obtained.

What is claimed is:

1. A compound of the formula

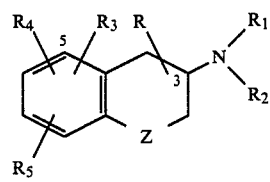

wherein Z represents S;

R represents hydrogen or lower alkyl; $R_1$ represents hydrogen, lower alkyl or aryl-lower alkyl; $R_2$ represents hydrogen, lower alkyl or aryl-lower alkyl; or $R_1$ and $R_2$ together represents alkylene of 4 to 6 carbon atoms; $R_3$ represents hydrogen, hydroxy, lower alkoxy, aryl-lower alkoxy, acyloxy or aryloxy; $R_4$ and $R_5$ represent independently hydrogen, lower alkyl or halogen; aryl within the above definitions represents phenyl or phenyl substituted by one to three of lower alkyl, halogen or lower alkoxy; acyloxy is hydroxy esterified in the form of a pharmaceutically acceptable ester; a mono or di-S-oxide thereof; or a pharmaceutically acceptable salt thereof.

2. A compound of claim 1 of the formula

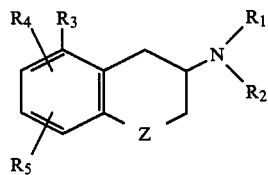

wherein Z represents S;

$R_1$ represents hydrogen, lower alkyl or aryl-lower alkyl; $R_2$ represents hydrogen, lower alkyl or aryl-lower alkyl; or $R_1$ and $R_2$ together represent alkylene of 4 to 6 carbon atoms; $R_3$ represents hydrogen, hydroxy, lower alkoxy, aryl-lower alkoxy; or $R_3$ represents hydroxy esterified in form of a pharmaceutically acceptable ester; $R_4$ and $R_5$ independently represent hydrogen, lower alkyl or halogen; aryl within the above definitions represents phenyl or phenyl substituted by one to three of lower alkyl, halogen or lower alkoxy; a mono or di-S-oxide thereof; or a pharmaceutically acceptable salt thereof.

3. A compound of claim 2 of formula IA wherein Z represents S; $R_1$ represents hydrogen or lower alkyl; $R_2$ represents lower alkyl or aryl-lower alkyl; or $R_1$ and $R_2$ together represent butylene or pentylene; $R_3$ represents hydroxy, lower aloxy or benzyloxy; or $R_3$ represents hydroxy esterified in form of a pharmaceutically acceptable ester; $R_4$ represents hydrogen, halogen or lower alkyl; $R_5$ represents hydrogen; or a pharmaceutically acceptable salt thereof.

4. A compound of claim 2 formula IA wherein Z represents S; $R_1$ and $R_2$ represent lower alkyl of 1 to 4 carbon atoms; $R_3$ represents hydroxy, lower alkoxy of 1 to 4 carbon atoms or benzyloxy; or $R_3$ represents hydroxy esterified in form of a pharmaceutically acceptable ester; $R_4$ is attached at the 7 or 8 position and represents hydrogen, lower alkyl of 1 to 4 carbon atoms or halogen; $R_5$ represents hydrogen; or a pharmaceutically acceptable salt thereof.

5. A compound of claim 1 of the formula

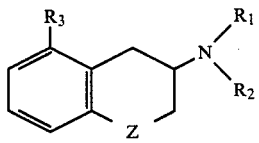

wherein Z represents S;

$R_1$ represents hydrogen or lower alkyl; $R_2$ represents lower alkyl, benzyl or phenethyl; $R_3$ represents hydroxy, lower alkoxy or benzyloxy; or $R_3$ represents hydroxy esterified in form of a pharmaceutically acceptable ester; or a pharmaceutically acceptable salt thereof.

6. A compound of claim 5 of formula IB wherein Z represents S; $R_1$ and $R_2$ are identical and represent straight chain alkyl of 1 to 4 carbon atoms; $R_3$ represents hydroxy or alkoxy of 1 to 4 carbon atoms; or a pharmaceutically acceptable salt thereof.

7. A compound of claim 5 being 3,4-dihydro-N,N-dipropyl-5-hydroxy-2H-benzothiopyran-3-amine or a pharmaceutically acceptable salt thereof.

8. A compound of claim 5 being 3,4-dihydro-N,N-dipropyl-5-ethyoxy-2H-benzothiopyran-3-amine or a phamraceuticaly acceptable salt thereof.

9. An antidepressant or anxiolytic pharmaceutical composition suitable for administration to a mammal comprising an effective amount of a serotonin recpetor stimulating compound of claim 1 in combination with one or more pharmaceutically acceptable carriers.

10. A method of treating anxiety or depression in mammals comprising the administration to a mammal in need thereof of an effective amount of a serotoinin receptor stimulating compound of claim 1 or of a pharmaceutical composition comprising said compound.

11. A method of treating central nervous system disorders responsive to the stimulation of serotonin central nervous system receptors in mammals, comprising the administration to a mammal in need thereof of a therapeutically effective amount of a compound of claim 1 or of a pharmaceutical composition comprising said compound.

* * * * *